(12) United States Patent
Kaphzan

(10) Patent No.: US 11,571,433 B2
(45) Date of Patent: Feb. 7, 2023

(54) METHODS FOR TREATING MEMORY IMPAIRMENT AND COGNITIVE DYSFUNCTION

(71) Applicant: CARMEL HAIFA UNIVERSITY ECONOMIC CORPORATION LTD., Haifa (IL)

(72) Inventor: Hanoch Kaphzan, Shimshit (IL)

(73) Assignee: CARMEL HAIFA UNIVERSITY ECONOMIC CORPORATION LTD., Haifa (IL)

( * ) Notice: Subject to any disclaimer, the term of this patent is extended or adjusted under 35 U.S.C. 154(b) by 58 days.

(21) Appl. No.: 16/975,129

(22) PCT Filed: Feb. 24, 2019

(86) PCT No.: PCT/IL2019/050207
§ 371 (c)(1),
(2) Date: Aug. 23, 2020

(87) PCT Pub. No.: WO2019/162945
PCT Pub. Date: Aug. 29, 2019

(65) Prior Publication Data
US 2021/0085693 A1    Mar. 25, 2021

Related U.S. Application Data

(60) Provisional application No. 62/634,256, filed on Feb. 23, 2018.

(51) Int. Cl.
*A61K 31/585* (2006.01)
*A61P 25/28* (2006.01)
*A61K 31/7048* (2006.01)

(52) U.S. Cl.
CPC ........ *A61K 31/585* (2013.01); *A61K 31/7048* (2013.01); *A61P 25/28* (2018.01)

(58) Field of Classification Search
CPC ... A61K 31/585; A61K 31/7048; A61P 25/00; A61P 25/28
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | Mcconnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |

FOREIGN PATENT DOCUMENTS

WO    2012075408 A1    6/2012

OTHER PUBLICATIONS

Kavirajan et al., Lancet Neurol 2007; 6; 782-92.*
Giralt (Human Molecular Genetics, 2012, vol. 21, No. 6, 1203-1216).*
Bachevalier, J. (1994). Medial temporal lobe structures and autism: A review of clinical and experimental findings. Neuropsychologia, 32(6), 627-648. doi:10.1016/0028-3932(94)90025-6.
Buckley, R. H. et al., (1998). Angelman syndrome: Are the estimates too low? American Journal of Medical Genetics, 80(4), 385-390. doi:10.1002/(sici)1096-8628(19981204)80:4<385::aid-ajmg15>3.0.co;2-9.
Chakraborty, D. et al., (2017). Selective ligands for Na + /K +-ATPase α isoforms differentially and cooperatively regulate excitability of pyramidal neurons in distinct brain regions. Neuropharmacology, 117, 338-351. doi:10.1016/j.neuropharm.2017.02.016.
DeLong, G. R. (1992). Autism, amnesia, hippocampus, and learning. Neuroscience & Biobehavioral Reviews, 16(1), 63-70 doi:10.1016/s0149-7634(05)80052-1.
Dickerson, B. C. et al., (2009). The Episodic Memory System: Neurocircuitry and Disorders. Neuropsychopharmacology, 35(1), 86-104. doi:10.1038/npp.2009.126.

(Continued)

*Primary Examiner* — Pancham Bakshi
(74) *Attorney, Agent, or Firm* — The Roy Gross Law Firm, LLC; Roy Gross

(57) ABSTRACT

The invention provides methods for treating a subject afflicted with a memory impairment or a cognitive dysfunction. Additional methods for improving memory and memory related functions in healthy subjects are also provided. The Methods include administration of an inhibitor of Na/K-ATPase.

6 Claims, 2 Drawing Sheets

(56) References Cited

OTHER PUBLICATIONS

Gustin, R. M. et al., (2010). Tissue-specific variation of Ube3a protein expression in rodents and in a mouse model of Angelman syndrome. Neurobiology of Disease, 39(3), 283-291. doi:10 1016/j.nbd 2010.04 012.

Jacobsen, J. et al., (1998). Molecular screening for proximal 15q abnormalities in a mentally retarded population. Journal of Medical Genetics, 35(7), 534-538. doi:10.1136/jmg.35.7.534.

Jiang, Y. et al., (1998). Mutation of the Angelman Ubiquitin Ligase in Mice Causes Increased Cytoplasmic p53 and Deficits of Contextual Learning and Long-Term Potentiation. Neuron, 21(4), 799-811. doi:10.1016/s0896-6273(00)80596-6.

Kaphzan, H. et al., (2011). Alterations in Intrinsic Membrane Properties and the Axon Initial Segment in a Mouse Model of Angelman Syndrome. Journal of Neuroscience, 31(48), 17637-17648. doi:10.1523/jneurosci.4162-11.2011.

Kaphzan, H. et al., (2013). Genetic Reduction of the α1 Subunit of Na/K-ATPase Corrects Multiple Hippocampal Phenotypes in Angelman Syndrome. Cell Reports, 4(3), 405-412. doi:10.1016/j.celrep.2013.07.005.

Kishino, T. et al., (1997). UBE3A/E6-AP mutations cause Angelman syndrome. Nature Genetics, 15(1), 70-73. doi:10.1038/ng0197-70.

Knoll, J. H. M. et al., (1989). Angelman and Prader-Willi syndromes share a common chromosome 15 deletion but differ in parental origin of the deletion. American Journal of Medical Genetics, 32(2), 285-290. doi:10.1002/ajmg.1320320235.

Lossie, A. C. (2001). Distinct phenotypes distinguish the molecular classes of Angelman syndrome. Journal of Medical Genetics, 38(12), 834-845. doi:10.1136/jmg.38.12.834.

Matsuura, T. et al., (1997). De novo truncating mutations in E6-AP ubiquitin-protein ligase gene (UBE3A) in Angelman syndrome. Nature Genetics, 15(1), 74 77. doi:10.1038/ng0197-74.

Petersen, R. C. (1995). Apolipoprotein E Status as a Predictor of the Development of Alzheimer's Disease in Memory-Impaired Individuals. JAMA: The Journal of the American Medical Association, 273(16), 1274. doi:10.1001/jama.1995.03520400044042.

Steffenburg, S. et al., (1996). Autism in Angelman syndrome: a population-based study. Pediatric Neurology, 14(2), 131-136. doi:10.1016/0887-8994(96)00011-2.

Sumiyoshi, C. et al., (2011). Impaired ability to organize information in individuals with autism spectrum disorders and their siblings. Neuroscience Research, 69(3), 252-257. doi:10.1016/j.neures.2010.11.007.

Sutcliffe, J. S. et al., (1997). Neuronally-expressed necdin gene: an imprinted candidate gene in Prader-Willi syndrome. The Lancet, 350(9090), 1520-1521. doi:10.1016/s0140-6736(05)63943-8.

Van Woerden, G. M. et al., (2007). Rescue of neurological deficits in a mouse model for Angelman syndrome by reduction of αCaMKII inhibitory phosphorylation. Nature Neuroscience, 10(3), 280-282. doi:10.1038/nn1845.

Williams, C. A. et al., (2006). Angelman syndrome 2005: Updated consensus for diagnostic criteria. American Journal of Medical Genetics Part A, 140A(5), 413-418. doi:10.1002/ajmg.a.31074.

PCT International Search Report for International Application No. PCT/IL2019/050207, dated May 22, 2019, 2 pp.

PCT Written Opinion for International Application No. PCT/IL2019/050207, dated May 22, 2019, 7 pp.

PCT International Preliminary Report for International Application No. PCT/IL2019/050207, dated May 22, 2019, 8 pp.

* cited by examiner

METHODS FOR TREATING MEMORY IMPAIRMENT AND COGNITIVE DYSFUNCTION

CROSS REFERENCE TO RELATED APPLICATIONS

This application is a National Phase of PCT Patent Application No. PCT/IL2019/050207 having International filing date of Feb. 24, 2019, which claims the benefit of priority under 35 U.S.C. § 119(e) to U.S. Provisional Patent Application No. 62/634,256 filed Feb. 23, 2018, entitled "METHODS FOR TREATING MEMORY IMPAIRMENT AND COGNITIVE DYSFUNCTION", the contents of which are incorporated herein by reference in their entirety.

FIELD OF INVENTION

Present embodiments relate to the treatment of memory impairment and cognitive dysfunction including methods for treating memory impairments and cognitive dysfunctions.

BACKGROUND OF THE INVENTION

Angelman syndrome (AS) is a human neuropsychiatric disorder associated with symptoms that include autism, mental retardation, motor abnormalities, epilepsy and lack of speech (Lossie et al., 2001; Williams et al., 2006). In most cases, AS is caused by the deletion of small portions on the maternal copy of chromosome 15, which includes the UBE3A gene (Kishino et al., 1997; Knoll et al., 1989; Matsuura et al., 1997; Sutcliffe et al., 1997). This phenomenon that only the maternal copy is expressed and the paternal allele is silenced, is called "imprinting", and in AS it occurs mainly in the brain (Gustin et al., 2010). The UBE3A gene encodes an enzyme termed ubiquitin ligase E3A (also termed E6-AP), which is one of a family of enzymes that covalently attaches polyubiquitin chains to proteins, to signal for their degradation by the 26S proteasome. The prevalence of AS is 1/10,000-1/12,000 births (Petersen et al., 1995; Steffenburg et al., 1996) and it constitutes about ~2-5% of all children with established developmental delay (Buckley et al., 1998; Jacobsen et al., 1998).

A mouse model of AS with UBE3A deletion has been generated and these mice exhibit susceptibility to epilepsy, impaired motor functioning, and cognitive abnormalities that correlate with neurological alterations observed in humans (Jiang et al., 1998). Like in other cases of autism (Bachevalier, 1994; DeLong, 1992; Dickerson and Eichenbaum, 2010; Sumiyoshi et al., 2011), one of the main brain regions that is implicated in AS in humans and in the mouse model is the hippocampus (Jiang et al., 1998). Hippocampus-dependent long-term memory (LTM) is impaired in these mice, and so is the cellular correlate of synaptic plasticity of hippocampal CA1 long-term potentiation in response to high frequency stimulation (HFS-LTP) (Jiang et al., 1998; van Woerden et al., 2007).

Hippocampal CA1 and CA3 pyramidal cells from AS mouse model exhibit increased expression of alpha1-Na/K-ATPase (a1-NaKA) and two axon initial segment (AIS) related proteins: NaV1.6 and ankyrin-G (Kaphzan et al., 2011).

Prevention of a1-NaKA increased expression in the hippocampus by genetic intervention rescues AS mice behavioral and electrophysiological hippocampal deficits (Kaphzan et al., 2013).

SUMMARY OF THE INVENTION

In one embodiment, the present invention provides a method for treating a subject afflicted with a memory impairment or a cognitive dysfunction, comprising administering to said subject an inhibitor of Na/K-ATPase, thereby treating a subject afflicted with a memory impairment or a cognitive dysfunction.

In another embodiment, the present invention provides a method for treating a subject afflicted with a memory impairment or a cognitive dysfunction, comprising administering to said subject an inhibitor of a1-NaKa, thereby treating a subject afflicted with a memory impairment or a cognitive dysfunction.

In another embodiment, the present invention provides a method for treating a subject afflicted with a memory impairment or a cognitive dysfunction, wherein the subject is further afflicted with a neurological disorder.

In another embodiment, the present invention provides a method for treating a subject afflicted with a memory impairment or a cognitive dysfunction, wherein the subject is afflicted with Angelman syndrome.

In another embodiment, the present invention provides a method for treating a subject afflicted with a memory impairment or a cognitive dysfunction, wherein the memory impairment comprises aberrant hippocampus-dependent long-term memory.

In another embodiment, the present invention provides a method for treating a subject afflicted with a memory impairment or a cognitive dysfunction, comprising administering to said subject an inhibitor of Na/K-ATPase, wherein the Na/K-ATPase inhibitor is selected from the list consisting of: *digitalis*, gitoxigenin, digoxigenin, digoxin, digitoxigenin, digitoxin, dihydrodigoxin, strophanthins, convallatoxin, cymarine, acetylstrophanthidin, strophanthidin, ouabagenin, ouabain, dihydroouabain, neriifolin, proscillaridin, proscillaridin A, cinobufagen, cinobufatolin, resibufagen, marinobufagenin, norbufalin, bufanolide, bufalin, and their respective isomers, inotropes, congeners, analogs, aglycone and metabolites.

In another embodiment, the present invention provides a method for treating a subject afflicted with a memory impairment or a cognitive dysfunction, comprising administering to said subject an inhibitor of Na/K-ATPase, wherein the Na/K-ATPase inhibitor is marinobufagenin.

In another embodiment, the method comprises administration of marinobufagenin in an amount from 0.5 µg/Kg/day to 1 mg/Kg/day.

In another embodiment, the method comprises administration of marinobufagenin in an amount from 5 µg/Kg/day to 50 µg/Kg/day.

In another embodiment, the duration of treatment is 14 days.

In another aspect, the present invention provides a method for improving memory or a memory related function in a subject in need thereof, comprising administering to said subject an inhibitor of Na/K-ATPase of Na/K-ATPase, thereby improving memory or a memory related function in a subject in need thereof.

In another embodiment, the present invention provides a method for improving memory or a memory related function in a subject in need thereof, wherein the memory related function is selected from: learning, reasoning, alertness, attention, concentration, language processing, and social learning.

In another embodiment, the present invention provides a method for improving memory or a memory related function in a subject in need thereof wherein memory is short-term memory or long-term memory.

DETAILED DESCRIPTION OF THE INVENTION

Figure 1:
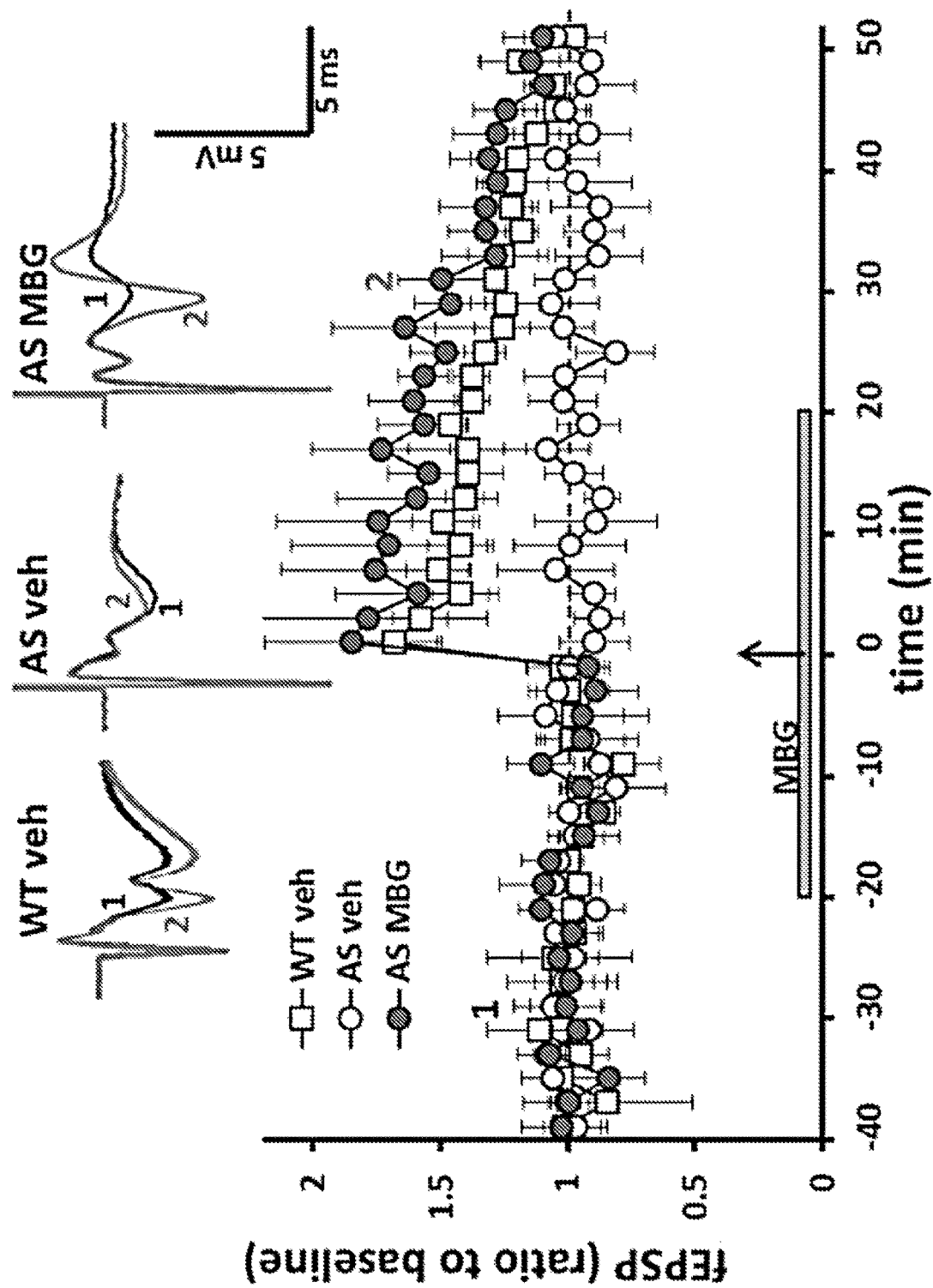
FIG. 1 is a graph showing correction of long-term potentiation defects in AS mice by administration of 0.5 µM marinobufagenin.

In one embodiment, provided a method for treating a subject with a memory impairment or a cognitive dysfunction comprising administering to the subject an agent that inhibits the activity of Na/K-ATPase.

In another embodiment, the term "subject" refers to a human having a condition of impairment of memory or cognitive dysfunction. In another embodiment, the term "subject" refers to a mammal such as a pet or a farm animal.

In another embodiment, the term "memory impairment" refers to a reduced ability to generate and retain memory. In another embodiment, the term "memory impairment" refers to a loss of existing memory. In another embodiment, the term "memory impairment" refers to a below average capacity to store memory for a short term and/or long term.

In another embodiment, the method of the present invention is used to improve a memory impairment in a subject in need thereof. In another embodiment, the improvement in memory is an improvement in at least one result of a memory assessment test. Memory assessment tests using methodologies from neuropsychology, human development and animal testing are well known in the art. Non-limiting examples of such tests are: visual short-term memory (VSTM), spatial working memory (SPWM), stroop task, attention blink, task switch, flanker task, visual search task, perceptual motor speed (PMS), digit Span and basic processing Speed.

In another embodiment, the term "cognitive dysfunction" as used herein, refers to a reduced ability of a subject to perceive, remember and act on information in the environment. In another embodiment, the method of the present invention is used to enhance at least one cognitive function in a subject in need thereof. In another embodiment, the enhancement of cognitive function is an improvement in at least one result of a cognitive function assessment test. Methods for cognitive function assessment of humans and other animals are well known in the art. Non-limiting examples of such methods are: inductive reasoning tests, inductive reasoning aptitude, intelligence quotient, situational judgement test, intelligence tests, Kohs block, Miller analogies test, Otis-Lennon School ability test, Raven's progressive matrices, Stanford-Binet IQ test, Wechsler adult intelligence scale, Wechsler intelligence scale for children, Wechsler preschool and primary scale of intelligence, wonderlic test, cambridge neuropsychological test automated battery, CDR computerized assessment system, cognitive bias, cognitive pretesting, cognitive process profile (CPP), draw-a-person test, knox cubes, modern language aptitude test, Pimsleur language aptitude battery, porteus maze test, consensus based assessment, knowledge organization, knowledge hierarchies, and knowledge Ontologies.

In another embodiment, memory improvement and/or cognitive function enhancement may be assessed by neuroscientific tools and methods. Non-limiting examples of such tools and methods are: functional MRI (fMRI), repetitive transcranial magnetic stimulation (rTMS), magnetoencephalography (MEG), positron emission tomography (PET) and electroencephalography (EEG), In another embodiment, the method of the present invention improves the results of a neuroscientific experiment of the subject as compared to pretreatment results.

In another embodiment, the method of the present invention is used for improving short-term memory in a subject in need thereof. The term "short-term memory" is known in the art as brief retention of information lasting from minutes to a few hours. In some embodiments, the improvement is an improvement of 5%-80% of short-term memory. In some embodiments, the improvement is an improvement of 5%-50% of short-term memory. In some embodiments, the improvement is an improvement of 5%-30% of short-term memory. In some embodiments, the improvement is an improvement of 5%-15% of short-term memory. In some embodiments, the improvement is an improvement of 30%-80% of short-term memory. In some embodiments, the improvement is an improvement of 50%-80% of short-term memory.

In another embodiment, the method of the present invention is used for improving long-term memory in a subject in need thereof. The term "long-term memory" is known in the art as the ability to retain information for long periods of days to years. In some embodiments, the improvement is an improvement of 5%-80% of long-term memory. In some embodiments, the improvement is an improvement of 5%-50% of long-term memory. In some embodiments, the improvement is an improvement of 5%-30% of long-term memory. In some embodiments, the improvement is an improvement of 30%-80% of long-term memory. In some embodiments, the improvement is an improvement of 50%-80% of long-term memory. In some embodiments, the improvement is an improvement of 5%-15% of long-term memory.

In another embodiment, the method of the present invention is used for enhancing a cognitive function in a subject in need thereof. In some embodiments, the enhancement is an enhancement of at least one cognitive function of 5%-80%. In some embodiments, the enhancement is an enhancement of at least one cognitive function of 5%-50%. In some embodiments, the enhancement is an enhancement of at least one cognitive function of 30%-80%. In some embodiments, the enhancement is an enhancement of at least one cognitive function of 50%-80%. In some embodiments, the enhancement is an enhancement of at least one cognitive function of 5%-30%. In some embodiments, the enhancement is an enhancement of at least one cognitive function of 5%-15%.

In another embodiment, the term "improvement" as used herein means an increment in the result of at least one memory assessment test when compared to pre-treatment results of the subject. In another embodiment, the improvement is compared to reference data. In another embodiment, the term "improvement" comprises enabling prolonging memory of a patient in need thereof. In another embodiment, the term "improvement" comprises enhancing the ability to memorize. In another embodiment, the term "improvement" comprises enhancing memory capacity.

In another embodiment, the term "enhancement" as used herein means an increment in the result of at least one cognitive function assessment test when compared to pre-treatment results of the subject. In another embodiment, the enhancement is compared to reference data.

The term "reference data" as used herein refers to results of memory tests and/or cognitive function tests of a defined population which serves as a standard for assessing the improvement of the treated subject.

In another embodiment, the method of the present invention is used in the treatment of diseases and/or pathologies that include and/or involve a memory impairment and/or a cognitive dysfunction. In another embodiment, the method of the present invention improves a memory impairment and/or a cognitive dysfunction in a subject suffering from a neurological condition. In another embodiment, the method of the present invention improves a memory impairment and/or a cognitive dysfunction in a subject suffering from a brain infection. In another embodiment, the method of the present invention improves a memory impairment and/or a cognitive dysfunction in a subject suffering from nutritional deficiencies. In another embodiment, the method of the present invention improves a memory impairment and/or a cognitive dysfunction in a subject suffering from age-associated memory impairment. In another embodiment, the method of the present invention improves a memory impairment and/or a cognitive dysfunction in a subject suffering from injuries of the brain. In another embodiment, the method of the present invention improves a memory impairment and/or a cognitive dysfunction in a subject suffering from adverse effects of a treatment to a medical condition such as, but not limited to, chemotherapy or radiotherapy for cancer treatment. In another embodiment, the method of the present invention improves a memory impairment and/or a cognitive dysfunction in a subject suffering a cognitive disorder.

In another embodiment, the method of the present invention inhibits deterioration in memory capacity. In another embodiment, the method of the present invention inhibits deterioration in memory duration. Deterioration refers to a decline in a result of at least one memory assessment test of the subject as compared to a previous measurement. In one embodiment, a subject susceptible to a memory impairment is treated according to the present methods. In another embodiment, a subject susceptible to a memory impairment is a subject afflicted with a neurological disorder such as Alzheimer's disease. In another embodiment, a subject susceptible to a memory impairment is a subject afflicted with a neurological disorder such as Angelman syndrome. In another embodiment, a subject susceptible to a memory impairment is a subject afflicted with a neurological disorder such as autism spectrum disorders. In another embodiment, a subject susceptible to a memory impairment is a subject afflicted with a neurological disorder such as Rett syndrome. In another embodiment, a subject susceptible to a memory impairment is a subject afflicted with a neurological disorder such as Huntington's disease.

In another embodiment, the term "treating" may include preventing, inhibiting or relieving a memory impairment and/or a cognitive dysfunction in a subject in need thereof by administering compounds as described herein.

In another embodiment, preventing relates to a subject that may be predisposed to memory impairment and/or cognitive dysfunction but does not yet experience or exhibit such symptoms.

In another embodiment, inhibiting memory impairment and/or a cognitive dysfunction refers to slowing or arresting their development in a subject exhibiting memory impairment and/or a cognitive dysfunction.

In another embodiment, relieving memory impairment or cognitive dysfunction in a subject having these symptoms refers to causing regression of the symptoms as compared to a previous measure of the subject. In some embodiments, the regression may be of 5%-80%. In some embodiments, the regression may be of 50%-80%. In some embodiments, the regression may be of 30%-80%. In some embodiments, the regression may be of 5%-50%. In some embodiments, the regression may be of 5%-30%. In some embodiments, the regression may be of 5%-15%.

In another embodiment, the term "administering" as used herein, includes delivery of a composition or one or more pharmaceutically active ingredients to a subject, by any appropriate methods, which serve to deliver the composition or its active ingredients or other pharmaceutically active ingredients to the subject. In another embodiment, the method of administration may vary depending on various factors, such as for example, the components of the pharmaceutical composition or the nature of the pharmaceutically active or inert ingredients, the site of the potential or actual malady, age and physical condition of the subject. Some non-limiting examples of ways to administer a composition or a pharmaceutically active ingredient to a subject include: oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

In another embodiment, the term "Na+/K+-ATPase" (sodium-potassium adenosine triphosphatase) as used herein and in the art, is an enzyme found in the plasma membrane of all animal cells. The Na+/K+ATPase enzyme is a solute pump that pumps sodium out of cells while pumping potassium into cells, against their concentration gradients. In another embodiment, compounds of the invention inhibit the activity of Na+/K+-ATPase. In another embodiment, compounds of the invention inhibit the amount of Na+/K+-ATPase. In another embodiment, compounds of the invention inhibit directly and/or indirectly the activity of Na+/K+-ATPase.

In another embodiment, the term "inhibitor" refers to any molecule which is capable of preventing or reducing the biochemical activity of Na+/K+-ATPase. Without being bound to any particular theory, the inhibition is achieved by a mechanism selected from: physical binding of the inhibitor to the target molecule thereby interfering with the activity of the target molecule, competing with the binding of substrates of the target molecule, preventing or reducing the expression of a protein target, interfering with the subcellular localization of the target molecule. In another embodiment, the Na+/K+-ATPase inhibitor is a competitive inhibitor. In another embodiment, the Na+/K+-ATPase inhibitor is a non-competitive inhibitor. In another embodiment, the Na+/K+-ATPase inhibitor is a selective inhibitor. In another embodiment, the Na+/K+-ATPase inhibitor is a non-selective inhibitor.

In another embodiment, the method comprises administering to the subject one or more compounds that inhibit Na+/K+-ATPase such as, but not limited to, "Cardiotonic steroids" (CTS). CTS include cardenolide or bufadienolide, or combination thereof. Non-limiting examples of cardenolides and bufadienolides are: *digitalis*, gitoxigenin, digoxigenin, digoxin, digitoxigenin, digitoxin, dihydrodigoxin, strophanthins, convallatoxin, cymarine, acetylstrophanthidin, strophanthidin, ouabagenin, ouabain, dihydrooubain, neriifolin, proscillaridin, proscillaridin A, cinobufagen, cinobufatolin, resibufagen, marinobufagenin, norbufalin, bufanolide, bufalin and similar compounds, and their respective isomers, inotropes, congeners, analogs, aglycone moieties and other variants, derivatives, equivalents, precursors and metabolites, and combination thereof.

In another embodiment, the term "a1-NaKa" (Sodium/potassium-transporting ATPase subunit alpha-1) as used herein, refers to an enzyme that in humans is encoded by the ATP1A1 gene (genebank accession number: NP_000692.2). Na+/K+-ATPase is composed of two subunits, a large catalytic subunit (alpha) and a smaller glycoprotein subunit (beta). There are four isoforms of the alpha subunit: a1-4. The a1 isoform is the common isoform that maintains Na and K gradients in all tissues.

In another embodiment, the method comprises administering to the subject a selective inhibitor of the a1 isoform of Na, K-ATPase. The term "selective inhibitor of the a1 isoform of Na, K-ATPase" means that the compound inhibits the a1 isoform of Na, K-ATPase to a greater degree than the other isoforms. In some embodiments, the selectivity of the compound for the a1 isoform of Na, K-ATPase is up to about 20 fold over other isoforms, e.g., up to 16 fold, 8 fold, 5 fold or 2 fold greater inhibition of the a1 isoform over other isoforms of this enzyme. As a non-limiting example, ouabain and digoxin are a3 inhibitors while Marinobufagenin is an a1 inhibitor.

In another embodiment, the selective inhibitor of the a1 isoform of Na, K-ATPase is marinobufagenin (MBG). In another embodiment, the selective inhibitor of the a1 isoform of Na, K-ATPase is resibufogenin.

In another embodiment, the subject suffering from memory impairment and/or a cognitive dysfunction is further afflicted with a neurological disorder. The term "neurological disorder" as used herein refers to any disorder of the nervous system that can result in a range of symptoms. According to some embodiment, the methods of the invention are used for treating a memory impairment and/or a cognitive dysfunction in a subject suffering from a neurological disorder. Non-limiting examples of neurological disorders that are treatable by the methods disclosed herein are selected from: Angelman syndrome, Rett syndrome, autism spectrum disorders, Alzheimer's disease, Huntington's disease, Lewy Body disease, dementia, cerebral atrophy, frontotemporal lobar degeneration, Pick's disease, multi-infarct dementia, Down's syndrome, neurotoxic injury, cerebral hypoxia/ischemia, traumatic brain injury, cholinergic hypofunction, vascular narrowing or blockage in the brain, decreased cerebral perfusion, neuroinflammation or cognitive disorders.

In some embodiments, the neurological disorder is a cognitive disorder. The term "cognitive disorder" as used herein refers to a condition that leads to cognitive dysfunction. Non-limiting examples of cognitive disorders include, but are not limited to: amnesia, dementia, and delirium, anxiety disorders, mood disorders, psychotic disorders, temporary hypoxia of the brain due to various reasons and mild cognitive impairment.

In another embodiment, the subject is afflicted with Angelman syndrome. The Term "Angelman syndrome" (AS) is known in the art as a genetic disorder that causes developmental disabilities and neurological problems, such as difficulty in speaking, balancing and walking, memory impairment and cognitive dysfunction. In another embodiment, the method is used to prevent memory impairment and/or a cognitive dysfunction in a subject afflicted with Angelman syndrome. In another embodiment, the method is used to inhibit memory impairment and/or a cognitive dysfunction in a subject afflicted with Angelman syndrome. In another embodiment, the method is used to relive memory impairment and/or a cognitive dysfunction in a subject afflicted with Angelman syndrome.

As used herein "Long-term memory" is a process that enables the brain to store information for long periods of time. The formation of long-term memory depends on a cellular process known in the art as long-term potentiation (LTP). Defects in LTP in the hippocampus may cause aberrant hippocampus-dependent long-term memory. In another embodiment, administration of compounds of the present invention increases hippocampal LTP, thereby improving hippocampus-dependent long-term memory in a subject in need thereof. In another embodiment, the increase in hippocampal LTP is in response to high frequency stimulation. The term "high frequency stimulation" as used herein refers to a biochemical assay for testing long-term potentiation described in the materials and methods section below.

In another embodiment, administration of 0.5 µg/Kg/day to 1 mg/Kg/day MBG results in a memory increase. In another embodiment, administration of 1 µg/Kg/day to 500 µg/Kg/day MBG results in a memory increase. In another embodiment, administration of 5 µg/Kg/day to 50 µg/Kg/day MBG results in a memory increase.

In some embodiments, a memory increase is an increase of 5% to 80% in hippocampus-dependent long-term memory formation. In another embodiment, a memory increase is an increase of 5% to 30% in hippocampus-dependent long-term memory formation. In another embodiment, a memory increase is an increase of 20% to 60% in hippocampus-dependent long-term memory formation. In another embodiment, a memory increase is an increase of 30% to 80% in hippocampus-dependent long-term memory formation. In another embodiment, a memory increase is an increase of 5% to 15% in hippocampus-dependent long-term memory formation.

In another embodiment, administration of Na/K-ATPase inhibitor increases LTP induction compared to base-line, wherein base line is determined as the LTP induction of an untreated or a mock treated subject as described in example 1. In some embodiments, an increase in LTP induction improves hippocampus-dependent long-term memory formation in a subject in need thereof.

In another embodiment, administration of Na/K-ATPase inhibitor increases neuronal excitability in the hippocampus of an AS afflicted subject thereby improving hippocampus-dependent long-term memory formation.

In another embodiment, administration of Na/K-ATPase inhibitor enhances synaptic plasticity in the hippocampus of an AS afflicted subject thereby improving hippocampus-dependent long-term memory formation.

In some embodiments, the method of the present invention is used for improving one or more membrane properties of pyramidal cells of the CA1 region in the hippocampus of an AS afflicted subject thereby improving hippocampus-dependent long-term memory formation of the subject. Methods for measuring membrane properties of CA1 pyramidal cells have been described by Kaphzan et al. 2013. In some embodiments, the method of the present invention improves at least one membrane property selected from: improvement in the resting membrane potential of CA1 pyramidal cells as described in example 2, improvement in membrane time constant, improvement in threshold potential, improvement in action potential amplitude and improvement in the maximal rise of action potential.

In another embodiment, the selective inhibitor of the a1 isoform of Na, K-ATPase is marinobufagenin (MBG) having the formula: 3-beta,5-dihydroxy-14,15-beta-epoxy-5-beta-bufa-20,22-dienolide.

In another embodiment, the duration of the treatment is between 24 h to 14 days. In another embodiment, the duration of the treatment is between 24 h to 30 days. In another embodiment, the duration of the treatment is between 1 to 12 months. In another embodiment, the method is used to treat a subject with a chronic need for improving a memory impairment or a cognitive dysfunction and the duration of the treatment is for the life time of the subject.

In another embodiment, the subject in need is a healthy human in need of improving memory or a memory related function such as, but not limited to, learning, reasoning, alertness, attention, concentration, language processing, social learning, or any combination thereof.

In another embodiment, the method is used to improve memory or a memory related function in a subject in need of improving learning skills. In another embodiment, the method is used to improve memory or a memory related function in a subject having to face ongoing mental fatigue. In another embodiment, the method is used to improve memory or a memory related function in a subject having to face mental daily stress. In another embodiment, the method is used to improve memory or a memory related function in a subject having to face occupational stress. In another embodiment, the method is used to improve memory or a memory related function in a subject having to face multi tasks activities. In another embodiment, the method is used to improve memory or a memory related function in a subject exhibiting memory loss caused by hormonal changes or imbalances. In another embodiment, the method is used to improve memory or a memory related function in a subject exhibiting transient memory loss. In another embodiment, the method is used to improve memory or a memory related function in a subject exhibiting age related memory loss.

In another embodiment, the method of the present invention is used to improve at least one memory related function in a subject in need thereof as measured by the methods of the present invention. In another embodiment, the improvement of a memory related function refers to an increased ability to perform a memory related function as compared to pre-treatment levels of the subject. In another embodiment, improvement is measured as compared to reference data.

As used herein, "learning" refers to an individual's ability of acquiring new knowledge, or modifying and reinforcing, long lost existing knowledge, behaviors, skills, values, or preferences and may involve synthesizing different types of information.

As used herein, "reasoning" refers to the use of reason, especially to form conclusions, inferences, or judgments.

As used herein, "alertness" refers to a state of active attention by high sensory awareness such as being watchful and prompt to meet danger or emergency, or being quick to perceive and act.

As used herein, "attention" refers to an individual's ability to focus on information that is relevant to a task at hand while ignoring information that is not relevant to the particular task.

As used herein, "concentration" refers to an individual's ability to direct one's thinking in whatever direction one would intend.

As used herein, "language processing" refers to the way humans use words to communicate ideas and feelings, and how such communications are processed and understood.

As used herein the term "social learning" relates to knowledge and skills obtained within a social context including for example observational learning, imitation, and modeling, and use of such information to serve as a guide for action on subsequent occasions.

In another embodiment, administration of 0.5 µg/Kg/day to 1 mg/Kg/day MBG results in improvement of memory or a memory related function. In another embodiment, administration of 1 µg/Kg/day to 500 µg/Kg/day MBG results in improvement of memory or a memory related function. In another embodiment, administration of 5 µg/Kg/day to 50 µg/Kg/day MBG results in in improvement of memory or a memory related function.

In some embodiments, an improvement of memory or a memory related function is an increase of 5% to 80% compared to pre-treatment levels of the subject. In some embodiments, an improvement of memory or a memory related function is an increase of 20% to 60% compared to pre-treatment levels of the subject. In some embodiments, an improvement of memory or a memory related function is an increase of 30% to 80% compared to pre-treatment levels of the subject. In some embodiments, an improvement of memory or a memory related function is an increase of 5% to 15% compared to pre-treatment levels of the subject.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods

Animals: Mice for experiments were bred from a female that was heterozygous for the deletion of Ube3a from a paternal origin (Ube3a p−/m+) and an α1-NaKA heterozygous male (α1-NaKA p−/m+). Both parents were on a C57/B16 background. For all experiments mice used were 8-12 weeks of age (unless otherwise specified), and for all experiments littermates were used as controls. Mice were genotyped using specific primers as described previously (Jiang et al., 1998) and (James et al., 1999).

Electrophysiology: Hippocampal slices were prepared from wild-type and AS model mice as previously described (Kaphzan et al., 2012; Kaphzan et al., 2013). LTP was induced in area CA1 with high frequency stimulation (HFS) by delivering two 100 Hz trains of HFS with an intertrain interval of 20 sec. The initial slope of the field excitatory postsynaptic potential (fEPSP) for each experiment was expressed as the ratio to the average baseline response prior to delivery of HFS.

Drug handling: Marinobufagenin was kept in stock solution (1 mg/10 ml) in 0.5% DMSO and was freshly diluted to the required concentration 0.042 mg/mL by saline prior to the experiment. At this stock concentration a volume of 100 μL for 16 days in a rate of 0.25 μL/hour correlated to approximately 10 μg/kg/day for a mouse of 25 grams. The exact concentration was calculated for each mouse according to its body weight. As a vehicle 1:200 stock solution of DMSO in water (the maximal concentration of DMSO matched to the maximal dose of MBG, i.e. 10 μg/kg/day) was used. For delivery via osmotic pumps only mice that weigh more than 20 g were used. For LTP studies, marinobufagenin was kept at 100 mM stock solution in DMSO and was freshly dissolved in 1:100,000 carboxygenated artificial cerebrospinal fluid to the final concentration of 1 μM. For chronic injections Alzet osmotic pumps filled with marinobufagenin were used as described (Elkareh et al., 2007; Fedorova et al., 2009; Kennedy et al., 2006; Liu et al., 2012; Yoshika et al., 2007).

Contextual fear conditioning: Mice were placed into a standard conditioning chamber and given a two-sec scrambled foot shock (0.75 mA) twice, two minutes and four minutes after session onset. The session ended 30 seconds after the second shock has been given. The occurrence of freezing was measured every 10 seconds throughout training. The mice were removed immediately and returned to their home cages. To test fear conditioning to the contextual cues, the mice were returned to the training context 24 hours after training for a five-minute test session. No shocks were presented during the test session. The occurrence of freezing was measured every 10 sec throughout testing.

Morris water maze: MWM experiments were performed as previously described (Kaphzan et al., 2013). The paradigm consisted of 6 days of training (reference phase), where the mice were trained to locate a submerged hidden platform. Mice were given four trials per day (each trial for 60 s maximum, inter-trial interval 60 min). On the 7th day, a single-probe trial (probe test) was given after removing the hidden platform from the pool. The day after (8th day), mice were tested using a similar paradigm to find the platform by using a visible cue (visible test). The escape platform marked by a visible cue was moved randomly between four locations. The animals' trajectories, escape latencies, number of previous platform position crossing, time spent in each quadrant, and swim speed were recorded with a computerized video-tracking system (Noldus EthoVision).

Real-time Calcium imaging: Calcium dynamics of CA1 pyramidal cells from WT and AS mice was assessed by a multiphoton imaging system with quasi-ratiometric calcium imaging. Following a single stimulus of Schaffer collaterals synaptic activation, the calcium concentrations dynamics were measured in a reactive spine of a CA1 pyramidal cell. Slices were placed in perfusion chamber on the stage of an upright microscope (Olympus BX-61 WI) and were held in place with a non-reactive plastic grid to avoid slice movement or field shift. To ensure prolonged viability of slices in imaging setup, slices were perfused with artificial CSF continuously bubbled with carboxygen gas mixture throughout the experiments. Fluo-5F and Alexa Fluor 594 were filled in a patch pipette and applied to the cells by whole cell configuration. Excitation was performed at 810 nm for two dyes Fluo-5F (green—calcium sensitive) and Alexa Fluor 594 (red—calcium insensitive) and the fluorescence dynamics was measured with a 500 Hz line scan of Fluo-5F green (520 nm) emission relative to the Alexa Fluor 594 emission (620 nm). Data was acquired and analyzed by using Olympus fluoview FV1200.

Example 1

HFS During MBG 0.5 μM Application Induces LTP Deficit Recovery in AS Mice

Application of 0.5 μM MBG induced a recovery of LTP deficit in the AS mice (FIG. 1). Hippocampal slices from WT and AS mice were stimulated with a single train of high frequency stimulation (1 sec 100 Hz-indicated by an arrow). Some of the AS slices were treated with either vehicle or MBG 0.5 μM 20 min before, during and 20 min after tetanization. WT vehicle: mice n=3, slices n=6; AS vehicle: mice n=2, slices n=4; AS MBG: mice n=2, slices n=4. P<0.05 for interaction of time and treatment in 2-way RM-ANOVA. Sample traces 1-baseline, 2-20 min after HFS. MBG did not affect baseline synaptic transmission. Inhibition of a1-NaKA with 0.5 μM MBG is partial and mild.

Example 2

Effect of MBG on Resting Membrane Potential of CA1 Pyramidal Cells

Figure 2:
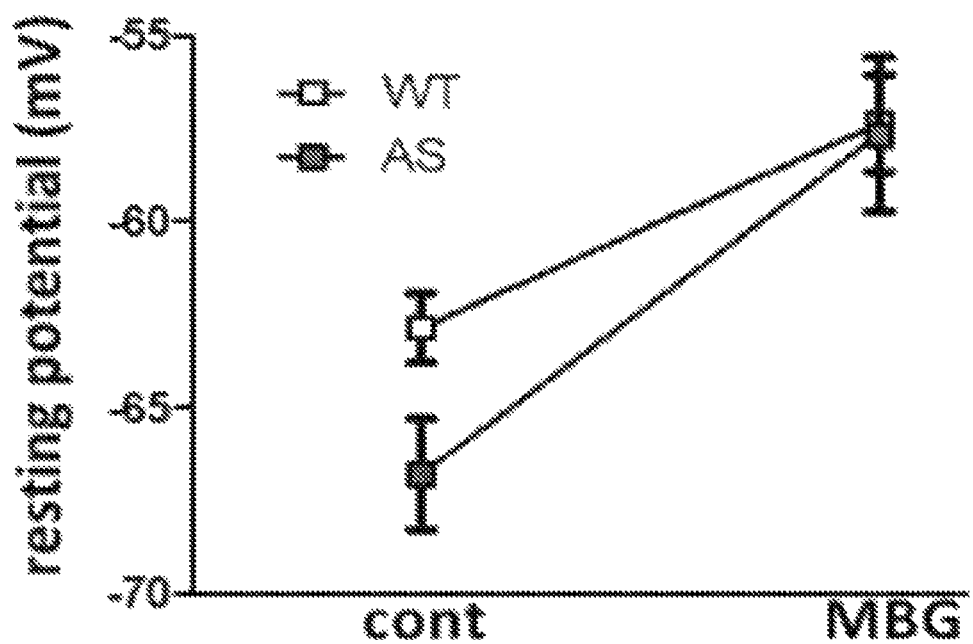
FIG. 2 is a graph showing the effect of administration of 10 µM marinobufagenin on resting membrane potential of CA1 pyramidal cells from the hippocampus of AS compared to WT mice.

The effect of a1-NaKA inhibition with MBG 10 μM on the resting membrane potential was tested (FIG. 2). Hippocampal slices were incubated for 10 min with MBG 10 μM. Whole cell recordings of CA1 pyramidal cells show a larger effect on the resting membrane potential of AS mouse compared to a WT littermate. WT 1 mouse, cells n=4. AS: 1 mouse cells n=5. P=0.07 for the interaction in 2 way RM-ANOVA. MBG induced a larger effect in AS mice than in wild-type littermates, thus supporting the assumption of an increased a1-NaKA activity Example 3

Chronic Inhibition of a1-NaKA Activity Rescues Hippocampal Dependent Memory in the AS Mice Osmotic pumps that chronically deliver 10 μg/kg/day MBG by intraperitoneal (IP) infusion are implanted to mice.

The MBG IP infusion starts 2 weeks before the initial contextual fear conditioning, and the memory testing is performed 24 hours after conditioning. Chronic IP infusion of MBG can correct the contextual fear memory deficit in AS model mice, 24 hours after training as described in the methods section. The infusions and experiments are performed in wild-type and AS mice littermates and MBG injected is compared to vehicle injection.

IP infusion of MBG 10 µg/kg/day corrects impaired contextual fear memory displayed by AS model mice. Such results are consistent with the idea that increased a1-NaKA activity causes hippocampal dependent memory deficits in the AS model mice. Next, an additional set of experiments is performed by employing Morris water maze paradigm, to demonstrate that this intervention can also rescue hippocampal dependent visuospatial memory. The AS model mice exhibit impaired visuospatial memory in the Morris water maze and this impairment is corrected by MBG.

Example 4

Chronic Inhibition of a1-NaKA Activity Rescues HFS-LTP in the AS Mice

Selective inhibition of a1-NaKA corrects the HFS-LTP impairment in AS mice hippocampus. Hippocampal slices from AS model mice and their wild-type littermates are incubated with MBG 1 µM and high frequency stimulation LTP is induced as described in the Methods section. While there is no effect on baseline synaptic transmission, there is a rescue of the impaired LTP phenotype of the AS hippocampal slices. This is consistent with the genetic a1-NaKA attenuation rescue.

What is claimed is:

1. A method for treating a subject afflicted with Angelman syndrome, the method comprising administering to said subject an inhibitor of Na/K-ATPase selected from the group consisting of: digitalis, gitoxigenin, digoxigenin, digoxin, digitoxigenin, digitoxin, dihydrodigoxin, strophanthins, convallatoxin, cymarine, acetylstrophanthidin, strophanthidin, ouabagenin, ouabain, dihydrooubain, neriifolin, proscillaridin, proscillaridin A, cinobufagen, cinobufatolin, resibufagen, marinobufagenin, norbufalin, bufanolide, and bufalin, thereby treating a subject afflicted with Angelman syndrome.

2. The method of claim 1, wherein said Na/K-ATPase is a1-NaKa.

3. The method of claim 1, wherein said inhibitor is marinobufagenin.

4. The method of claim 3, wherein said marinobufagenin is administered in an amount from 0.5 µg/Kg/day to 1 mg/Kg/day.

5. The method of claim 3, wherein said marinobufagenin is administered in an amount from 5 µg/Kg/day to 50 µg/Kg/day.

6. The method of claim 1, wherein the duration of treatment is 14 days.

* * * * *